(12) United States Patent
Bernstein

(10) Patent No.: US 8,668,693 B2
(45) Date of Patent: Mar. 11, 2014

(54) FIXATION DEVICE FOR PROXIMAL ELBOW FRACTURES AND METHOD OF USING SAME

(76) Inventor: Richard A. Bernstein, Woodbridge, CT (US)

(*) Notice: Subject to any disclaimer, the term of this patent is extended or adjusted under 35 U.S.C. 154(b) by 1612 days.

(21) Appl. No.: 11/760,113

(22) Filed: Jun. 8, 2007

(65) Prior Publication Data

US 2008/0306479 A1   Dec. 11, 2008

(51) Int. Cl.
*A61B 17/58* (2006.01)

(52) U.S. Cl.
USPC ............................................................ 606/64

(58) Field of Classification Search
USPC .................................... 606/62–68, 280–331
See application file for complete search history.

(56) References Cited

U.S. PATENT DOCUMENTS

| | | | | |
|---|---|---|---|---|
| 3,497,953 A | * | 3/1970 | Weissman | 433/173 |
| 5,810,820 A | * | 9/1998 | Santori et al. | 606/63 |
| 5,931,839 A | * | 8/1999 | Medoff | 606/286 |
| 5,971,986 A | * | 10/1999 | Santori et al. | 606/62 |
| 6,348,052 B1 | * | 2/2002 | Sammarco | 606/284 |
| 6,558,388 B1 | * | 5/2003 | Bartsch et al. | 606/62 |
| 6,706,046 B2 | | 3/2004 | Orbay et al. | |
| 6,730,090 B2 | | 5/2004 | Orbay et al. | |
| 6,926,720 B2 | | 8/2005 | Castaneda | |
| 7,029,476 B2 | * | 4/2006 | Hansson | 606/304 |
| 2004/0210220 A1 | * | 10/2004 | Tornier | 606/69 |
| 2006/0106385 A1 | * | 5/2006 | Pennig | 606/64 |
| 2006/0116679 A1 | * | 6/2006 | Lutz et al. | 606/69 |
| 2006/0264951 A1 | * | 11/2006 | Nelson et al. | 606/72 |

* cited by examiner

*Primary Examiner* — Kevin T Truong
*Assistant Examiner* — Michael Araj
(74) *Attorney, Agent, or Firm* — F. Chau & Associates, LLC

(57) ABSTRACT

A bone fixation device includes a rod including a first portion extending from a proximal side of the rod, and a second portion extending from the first portion, wherein the rod is inserted into a medullary canal of an ulna bone, the first portion includes a plurality of longitudinally displaced screw holes, having axes whereby at least two screws inserted into the screw holes extend in discrete directions into a metaphyseal portion of the ulna. The bone fixation device also includes a curved extension portion extending from the proximal side of the rod to capture an olecranon of the ulna. The device provides the benefits of an intramedullary nail and proximal tension band type fixation in a single device. The fixation device permits a minimally invasive treatment of proximal ulna fractures that may otherwise be under treated.

17 Claims, 4 Drawing Sheets

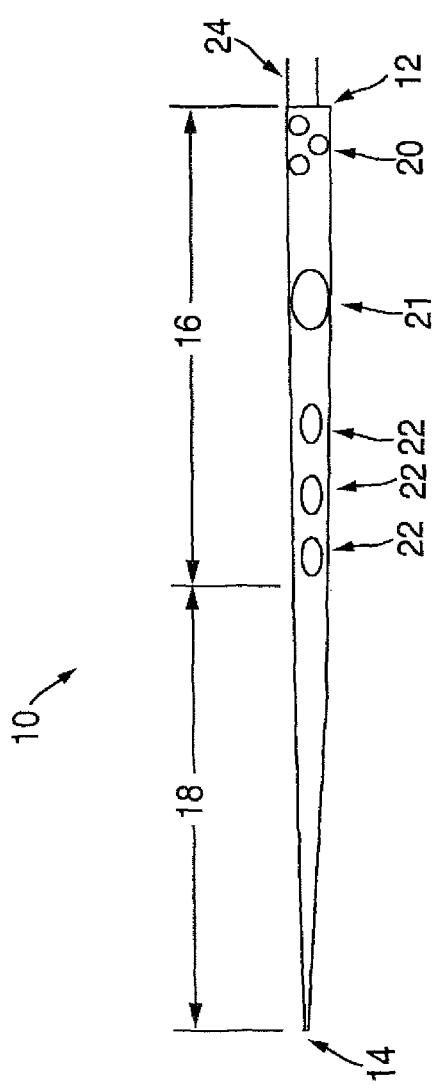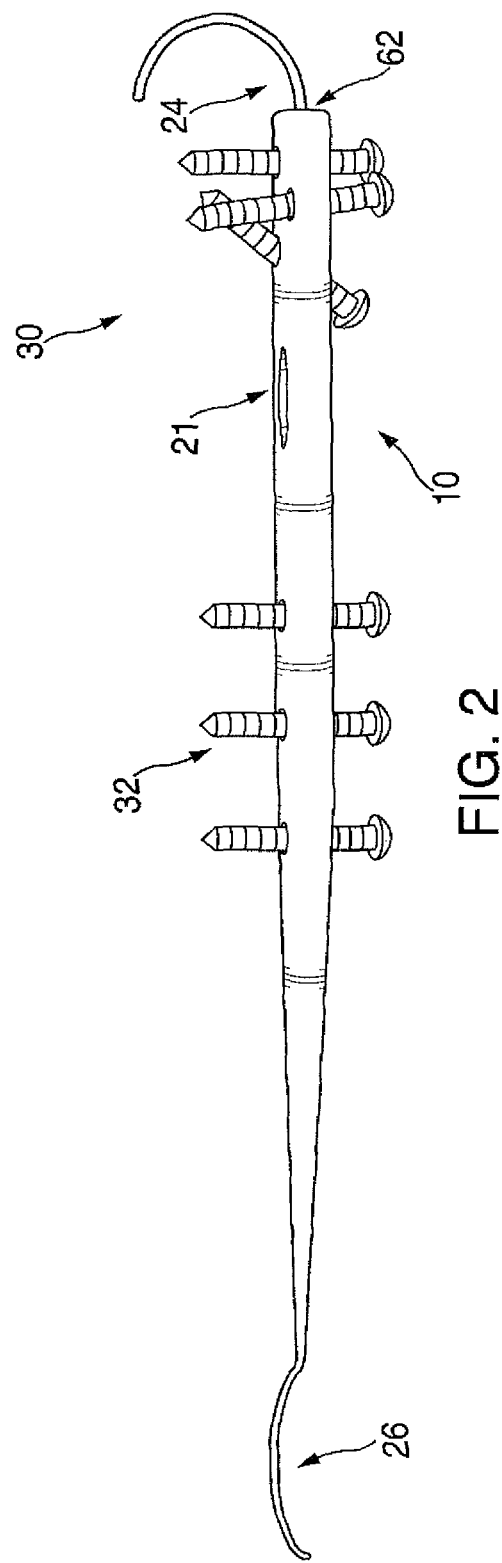

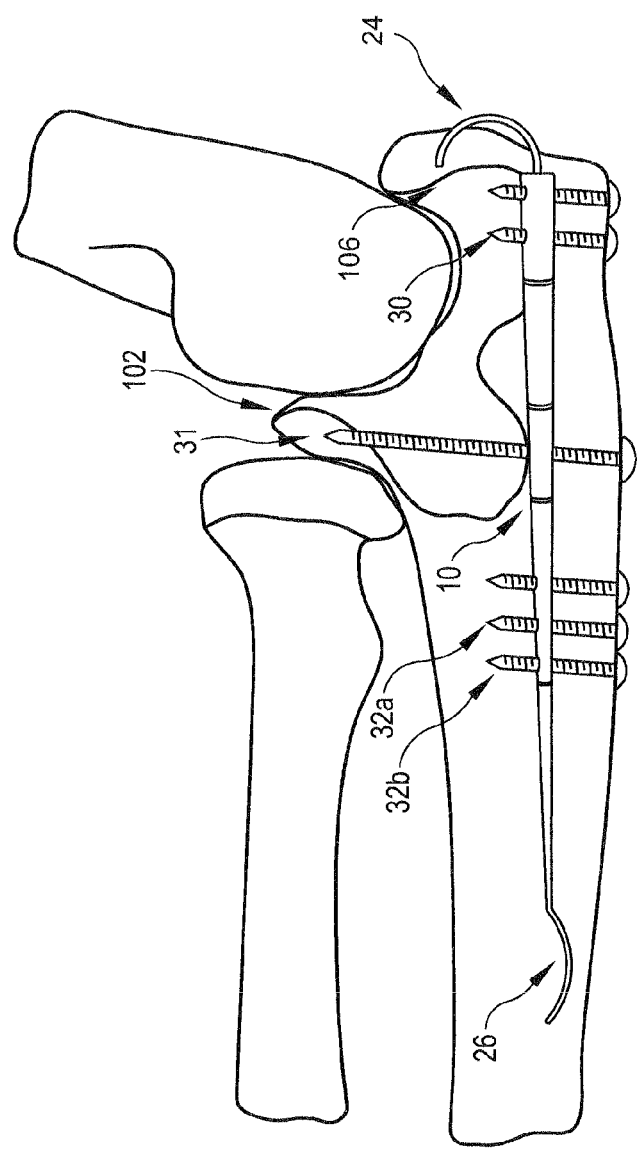
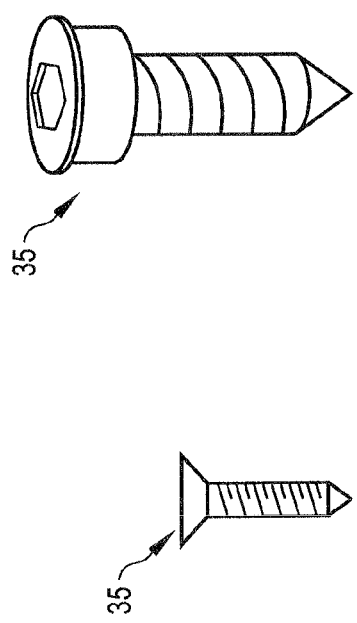
FIG. 3
FIG. 4a
FIG. 4b
FIG. 4c

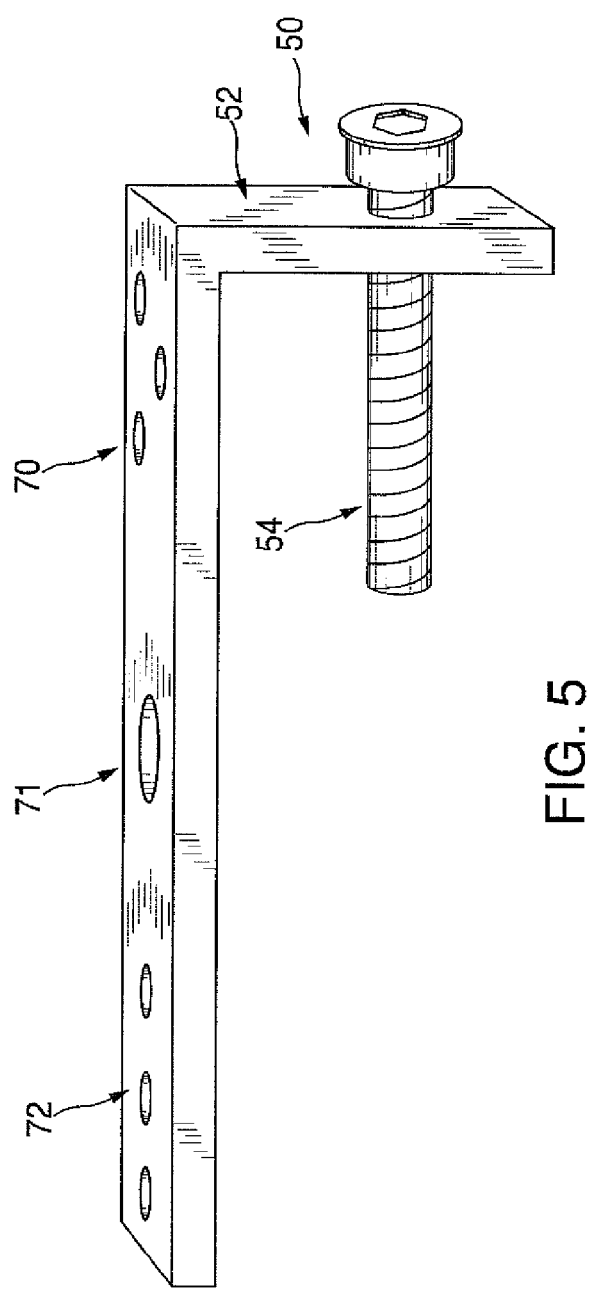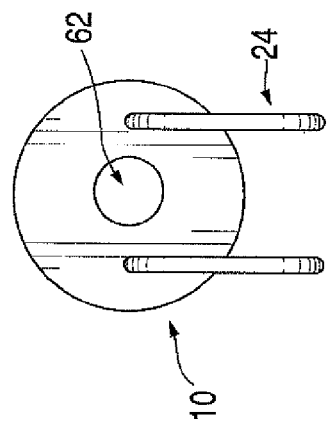

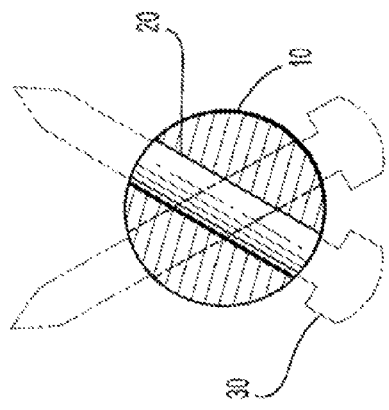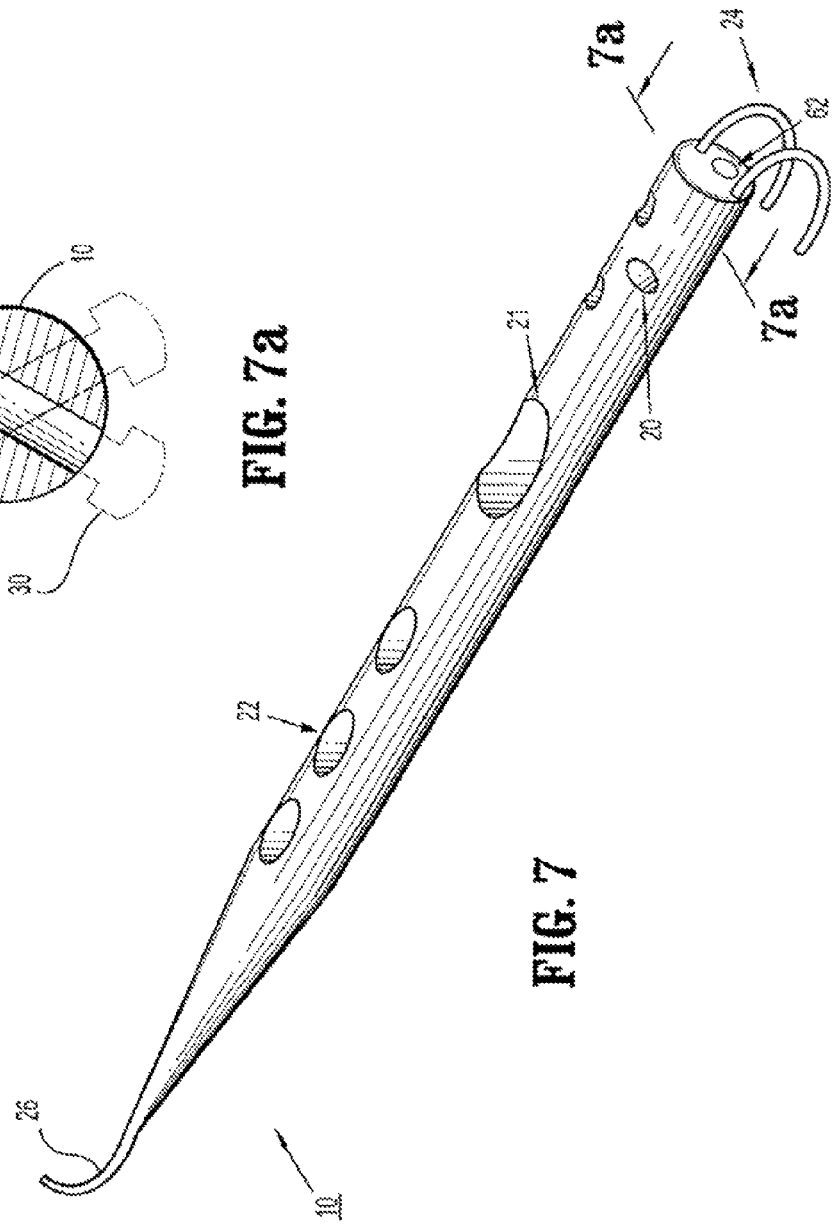

FIXATION DEVICE FOR PROXIMAL ELBOW FRACTURES AND METHOD OF USING SAME

BACKGROUND OF THE INVENTION

1. Technical Field

The present disclosure relates to surgical devices for bone fractures, and, more particularly, to implants for the fixation of proximal elbow fractures in the ulna.

2. Discussion of the Related Art

Conventional devices for treating fractures of the proximal ulna and olecranon use extramedullary plating systems or a combination of pins/screws and a tension band wire. These conventional devices and systems cause hardware irritation, loosening and backing out of hardware, and are bulky. The current techniques, involving placement of a plate outside of the bone or a series of wires within and around the bone, can irritate the skin and necessitate a second surgical procedure for removal.

In addition, there is no minimally invasive procedure to treat fractures occurring at the metaphysis and that also provides the desired immobilization for such fractures.

Furthermore, there is no minimally invasive procedure to treat proximal ulna fractures that provides the stability generally obtained by more invasive procedures, such as open reduction and internal fixation.

Therefore, a need exists for an intramedullary rod to treat fractures of proximal ulna/olecranon in a less invasive manner, while minimizing hardware irritation and achieving better fracture fixation.

SUMMARY OF THE INVENTION

Embodiments of the present invention provide a minimally invasive treatment, which provides stabilization and support to ulna fractures and to fractures occurring at the metaphysis, while using less prominent hardware, achieving better fracture fixation and better healing with a lower secondary operation rate than other implants.

A bone fixation device, in accordance with an embodiment of the present invention, comprises a proximal portion including a plurality of longitudinally displaced screw holes, and a proximal bent extension portion for capturing an olecranon.

The bent extension portion may be selectively removed from the fixation device, and may include at least one of a wire or a pin. The proximal portion may have a substantially circular cross section.

A bone fixation device, in accordance with an embodiment of the present invention, comprises a first portion extending from a proximal side of the fixation device including a plurality of screw holes, and a hole for receiving a screw to capture a coronoid process.

Each of the plurality of screw holes may be oriented at a different angle with respect to a longitudinal axis of the first portion. A second tapered portion may extend from the first portion.

The hole for receiving the screw to capture the coronoid process may be elliptical.

A bone fixation device for use with a plurality of screws each having a threaded head portion, in accordance with an embodiment of the present invention, comprises a plurality of threaded screw holes for receiving the plurality of screws, wherein the threaded screw holes define axes to provide the screws inserted into the screw holes in an arrangement in which at least two of the screws extend in discrete directions.

The screw holes may be arranged such that each of the screws extends in a discrete direction.

A bone fixation device for use in a bone having a diaphyseal portion and a metaphyseal portion and having a fracture at or adjacent the metaphyseal portion, in accordance with an embodiment of the present invention, comprises a metaphyseal part adapted to receive and orient screws in discrete planes, a diaphyseal part adapted to receive screws for fixing the diaphyseal part to the diaphyseal portion, a curved portion to capture a proximal fragment of the bone, wherein the curved portion extends from the metaphyseal part.

The curved portion may be removable, and the device may occupy a strictly intramedullary position in the bone upon removal of the curved portion.

The metaphyseal part may be substantially rigid and substantially straight, and may include a plurality of longitudinally displaced screw holes each oriented in a discrete direction. The diaphyseal part may include a relatively flexible section sized to be inserted into a medullary canal of an ulna bone, and may include a hole for receiving a screw to capture the coronoid process.

A bone fixation device, in accordance with an embodiment of the present invention, comprises a rod including a first portion extending from a proximal side of the rod, and a second portion extending from the first portion, wherein the rod is inserted into a medullary canal of an ulna bone, the first portion includes a plurality of longitudinally displaced screw holes having axes whereby at least two screws inserted into the screw holes extend in discrete directions into a metaphyseal portion of the ulna.

A curved extension portion may extend from the proximal side of the rod to capture an olecranon of the ulna. A hole may be provided in the first portion for receiving a screw to capture a coronoid process of the ulna.

The device may include at least one screw hole for receiving a screw into a diaphyseal portion of the ulna. The screw may be unicortical or bicortical, locked or unlocked, and may include a countersunk head.

BRIEF DESCRIPTION OF THE DRAWINGS

Exemplary embodiments of the present invention will be described below in more detail, with reference to the accompanying drawings:

FIG. 1 is a top view of an intramedullary fixation device, according to an embodiment of the present invention;

FIG. 2 is a schematic side view of an intramedullary fixation device, according to an embodiment of the present invention;

FIG. 3 is a schematic view of an intramedullary fixation device implanted at a proximal portion of the ulna, according to an embodiment of the present invention;

FIG. 4 shows screws having countersunk heads, according to an embodiment of the present invention;

FIG. 5 shows a schematic side view of a jig for use with an intramedullary fixation device, according to an embodiment of the present invention;

FIG. 6 shows an end on view of an intramedullary fixation device at location where a jig is attached, according to an embodiment of the present invention;

FIG. 7 is a perspective top view of an intramedullary fixation device, according to an embodiment of the present invention; and FIG. 7a is a cross-sectional view of a portion of FIG. 7 for illustrating orientations of screws and screw holes.

DETAILED DESCRIPTION OF EXEMPLARY EMBODIMENTS

Exemplary embodiments of the present invention now will be described more fully hereinafter with reference to the accompanying drawings. This invention may, however, be embodied in many different forms and should not be construed as limited to the embodiments set forth herein.

Turning now to FIGS. 1-3 and 7, a fixation device, particularly an intramedullary rod 10, is provided which includes a first portion 16 adjacent a proximal side 12 of the rod 10 and a second portion 18 adjacent a distal side 14 of the rod 10. The rod 10 is used for treatment of proximal ulna fractures.

It is to be understood that the use of the terms "first and second portions 16, 18" are not meant to limit the rod 10 to being formed in two separate parts. The terms have been introduced for purposes of description to describe parts of the rod 10. The rod 10 is preferably formed as a continuous member from end to end. However, in alternative embodiments, the rod 10 may include the first and second portions 16, 18 which are separately formed, made from the same or different materials, and joined together prior to use.

The rod 10, including the first and second portions 16, 18, may be rigid, straight and substantially circular in cross section. Alternatively, the entire rod 10 or portions thereof may be flexible, curved and/or tapered. For example, as shown in FIGS. 1 and 7, the second portion 18 may be tapered, and may be flexible to facilitate insertion into the bone. In addition, the cross-section of the rod 10 or portions thereof is not limited to being circular, and may be, for example, oval, rectangular, square, and/or another shape that is compatible with the use of the rod 10.

Referring to FIGS. 1 and 7, the first portion 16 of the rod 10 includes a plurality of (e.g., three (3)) longitudinally displaced (displaced along a length of the rod 10) threaded screw holes 20, each of which is adapted to position a screw 30, for example, a screw having a threaded head portion, in a different position from the remaining screws 30. For example, referring to FIGS. 1 and 7, the holes 20 may be in a triangular arrangement. Alternatively, as shown in FIG. 2, the holes may be in a linear arrangement.

Further, the axis of each hole 20 may have a distinct orientation relative to the axes of the remaining holes 20. That is, the screws 30 are in a fanned arrangement. For example, referring to FIG. 7a, the angle of each hole 20 can be different with respect to the longitudinal axis of the rod 10. Alternatively, any two or more holes 20 and consequently, the screws 30, can be oriented at the same angle, for example, perpendicular relative to the longitudinal axis of the rod 10.

The screws 30 can be screwed into the olecranon 106 or the portion of the ulna 100 adjacent the olecranon 106. The number of screw holes 20 may be more or less than three. Holes are drilled through the screw holes 20 and into the metaphyseal portion of the bone 100, and screws 30 are introduced through the holes to provide stabilization and support for the fracture fragments.

The proximal side 12 of the rod 10 can include a pre-bent extension portion 24, including for example, a pre-bent curved pin extension (e.g., a 0.062 inch pre-bent pin extension, or pair of curved 2 mm pins/wires), and/or pre-bent wires extending therefrom to capture the proximal fragment of the ulna 100. The extension portion 24 to, for example, purchase the olecranon process, can be removable by a surgeon's discretion after the rod 10 has been implanted.

The first portion 16 also includes a screw hole 21 for receiving a coronoid screw 31 to, if necessary, capture a coronoid fragment and stabilize the coronoid process 102 of the ulna 100. The hole 21 may be elliptical or the diameter of a circular hole 21 is large enough to permit adjustment of the angle of the coronoid screw 31. For example, the angle of the coronoid screw may be any angle along about a 45 degree arc in any direction from perpendicular to the rod 10. To the extent required, additional screw holes 21 for receiving more than one coronoid screw 31 may be provided.

The first portion 16 also includes a plurality of (e.g., three (3)) threaded cortical screw holes 22 for receiving cortical screws 32a and 32b. The number of cortical screw holes 22 may be more or less than three. As shown in FIG. 3, in an alternative embodiment, the cortical screw holes 22 may be provided in both the first and second portions 16, 18 of the rod 10, and in tapered and/or untapered portions. According to an embodiment, screw holes 22 may be provided entirely in a tapered portion or entirely in an untapered portion. Referring to FIG. 3, the cortical screws may be bicortical screws 32a or unicortical screws 32b. Unicortical screws go through one cortex of the bone and can lock on the rod 10. Bicortical screws are long enough to go through the rod and extend to get fixation through both cortices of the bone. Further, the screws 32a, 32b may be locked (e.g., locking in the rod 10) or unlocked. Depending, for example, on the type of repair required, any combination of unicortical and/or bicortical and locked and/or unlocked screws can be used.

Referring to FIG. 4, according to an embodiment, the screws 30 (which have also been described as having a threaded head), 31, 32a and/or 32b may include countersunk screw heads 35 (as shown in (a), (b) and (c)) so as to allow the screws 30, 31, 32a and 32b to sink into the bone into which they are being screwed. Referring to FIG. 3, the countersunk screws are non-prominent in the bone, thereby reducing irritation and bulk. Any one, combination or all of the described screw types can include a countersunk head.

The distal side 14 of the rod 10 can include a curved extension portion 26 used to centralize the rod 10 in the medullary canal 104. According to an embodiment, the first portion 16 may taper in diameter into the second portion 18. According to an embodiment, the second portion may be angled with respect to the first portion 16. According to an embodiment, the diameter of the cross-section of the first portion 16 is larger than the largest diameter of the cross-section of the second portion 18.

In use, a small incision (generally less than 1 cm) is made in the skin, for example, at the tip of the olecranon 106. An awl is then introduced in the ulna 100 to accept the rod 10. The second portion 18 including the tapered end is introduced percutaneously through the incision and through the fracture location into the medullary canal 104 of the bone 100. The rod 10 is then maneuvered against the proximal surface of the olecranon 106 capturing the fragment of the olecranon 106 with the prebent extension portion 24, including, for example, pins or wires 24.

It is appreciated that reduction of the fracture may occur at this stage or at any other medically reasonable time during the fracture fixation process. During introduction into the bone 100 and when implanted in the bone 100, the second portion including the tapered and flexible section may undergo some degree of bending, as the medullary canal 104 may not be perfectly straight.

In accordance with the embodiments of the present invention, the rod 10 provides multiple point fixation along the canal 104 with screws 30, 31 and 32a, 32b, and tension type fixation with extension portion 24. The rod 10 can provide multiplanar fixation in cancellous bone.

The screws 30, 31, 32a, 32b are preferably inserted through puncture holes in the skin, into the bone, and into screw holes 20, 21 and 22 to further fix the rod 10. Holes to receive the screws 32a, 32b are drilled in a locking or non-locking manner into the ulna 100 in the diaphyseal area. Optionally, locked or unlocked, and bicortical or unicortical screws 32a, 32b may be provided into the diaphyseal portion of the bone 100 to further fix the rod.

The holes can be drilled in a gliding fashion to impact the fracture further. The screws 30, 31, 32a, 32b are introduced through the puncture holes in the skin, into the screw holes 20, 21 and 22 and the holes drilled in the bone.

A guide can be used to locate the positions of screw holes. A drill guide can provide oblique intramedullary fixation, as opposed to fixation under the surface of the bone. Referring to FIG. 5, a jig 50 is shown. The jig 50 includes a vertical portion 52 and a horizontal portion 51. Referring to FIGS. 2 and 5-7, the jig 50 may be attached to the rod 10 by screwing a locking screw 54 attached at an end of the vertical portion 52 into a threaded hole 62 formed in an end of the rod 10. The threaded hole 62 extends in a lengthwise direction of the rod 10, and is formed so as not to interfere with holes 20 formed in the rod 10. Accordingly, when the jig 50 is attached to the rod 10, the horizontal portion 51 of the jig 50 is parallel or substantially parallel to the rod 10 and the locking screw is also parallel or substantially parallel to the rod 10. The locking screw 54 includes threads to mate with the threads in the threaded hole 62.

The horizontal portion 51 of the jig 50 includes a plurality of guide holes 70, 71 and 72 that correspond to any one or more of the holes 20, 21 and 22 formed in the rod 10. The guide holes 70 in the horizontal portion 51 of the jig 50 may be angled to correspond to the angle of the holes 20 with respect to the longitudinal axis of the rod 10. The guide holes in the horizontal portion 51 function as drill guides and have a diameter to receive a drill for drilling holes into the bone that correspond to the holes 20, 21 and 22. If the guide holes are angled, the resulting drill guides are angled so that angled holes may be drilled into the bone. In addition the guide holes function as screw guides through which the screws 30, 31, 32a and 32b may be run for placement through the holes 20, 21 and 22 and into the bone. The guide holes in the horizontal portion 51 may be threaded to receive attachments that function as the drill and screw guides.

The vertical and horizontal portions 52, 51 of the jig 50 may be interchangeable with different sized portions, and/or portions having a different set of guide holes to correspond to a different hole configuration on a rod 10. According to an embodiment, the vertical and horizontal portions 52, 51 can be integrally formed as one piece. In use, the jig 50 can be entirely outside of the bone because the screws do not affix or lock into an extramedullary plate.

The rod 10 provides the benefits of both an intramedullary nail and tension band in a single device. The rod 10 permits a minimally invasive treatment of ulna fractures that may otherwise be under treated.

The rod 10 is preferably made of metal, for example, titanium or stainless steel, or other biocompatible materials. Also, while the screws 30 are preferably fanned, other arrangements can be used.

It will also be appreciated that while particular dimensions may have been disclosed, other dimensions may be used as well.

Although exemplary embodiments of the present invention have been described hereinabove, it should be understood that the present invention is not limited to these embodiments, but may be modified by those skilled in the art without departing from the spirit and scope of the present invention, as defined in the appended claims.

What is claimed is:

1. A bone fixation device for use in a bone having a diaphyseal portion and a metaphyseal portion and having a fracture at or adjacent the metaphyseal portion, the device comprising:
    a metaphyseal part adapted to receive and orient screws in discrete planes;
    a diaphyseal part adapted to receive screws for fixing the diaphyseal part to the diaphyseal portion; and
    a pre-bent extension portion extending beyond an intramedullary space to capture a proximal fragment of the bone, wherein the pre-bent extension portion extends from the metaphyseal part, and includes at least one of a bent wire or a bent pin, wherein the metaphyseal part and the pre-bent extension portion are dimensioned, shaped and positioned to capture the proximal fragment of the bone.

2. The bone fixation device of claim 1, wherein the pre-bent extension portion is removable, and the device occupies a strictly intramedullary position in the bone upon removal of the curved portion.

3. The bone fixation device of claim 1, wherein the metaphyseal part is substantially rigid and substantially straight.

4. The bone fixation device of claim 1, wherein the diaphyseal part includes a relatively flexible section sized to be inserted into a medullary canal of an ulna bone.

5. The bone fixation device of claim 1, wherein the metaphyseal part includes a plurality of longitudinally displaced screw holes.

6. The bone fixation device of claim 1, wherein a plurality of screw holes are each oriented in discrete directions.

7. The bone fixation device of claim 4, further comprising a hole in the diaphyseal part for receiving a screw to capture a coronoid process.

8. The bone fixation device of claim 1, further comprising an extension portion extending from the diaphyseal part for centralizing the device in a medullary canal.

9. The bone fixation device of claim 1, wherein an outer surface of the device is substantially free of protrusions prior to and after deployment of the device in a medullary canal.

10. A bone fixation device, comprising:
    a rod including a first portion extending from a proximal side of the rod, and a second portion extending from the first portion, wherein:
    the rod is for insertion into a medullary canal of an ulna bone;
    the first portion includes a plurality of longitudinally displaced screw holes having axes whereby at least two screws inserted into the screw holes are configured to extend in discrete directions into a metaphyseal portion of the ulna;
    a curved extension portion extending from the proximal side of the rod to capture a proximal fragment of an olecranon of the ulna, wherein the curved extension portion includes at least one of a bent wire or a bent pin, and wherein the proximal side of the rod and the curved extension portion are dimensioned, shaped and positioned to capture the proximal fragment of the olecranon of the ulna.

11. The bone fixation device of claim 10, further comprising a hole in the first portion for receiving a screw to capture a coronoid process of the ulna.

12. The bone fixation device of claim 10, further comprising at least one screw hole for receiving a screw into a diaphyseal portion of the ulna.

13. The bone fixation device of claim 12, wherein the screw for insertion into the diaphyseal portion is unicortical or bicortical.

14. The bone fixation device of claim 12, wherein the screw for insertion into the diaphyseal portion is locked or unlocked.

15. The bone fixation device of claim 12, wherein the screw for insertion into the diaphyseal portion includes a countersunk head.

16. The bone fixation device of claim 10, further comprising an extension portion extending from the second portion for centralizing the rod in the medullary canal.

17. The bone fixation device of claim 10, wherein an outer surface of the rod is substantially free of protrusions prior to and after deployment of the rod in the medullary canal.

* * * * *